United States Patent [19]
Zaglio

[11] Patent Number: 5,033,852
[45] Date of Patent: Jul. 23, 1991

[54] OPTICAL MEASURING DEVICE FOR MEASURING THE FAT CONTENTS OF MILK

[76] Inventor: Enrico Zaglio, Via G. B. da Farfengo 52, 25127 Brescia, Italy

[21] Appl. No.: 494,167

[22] Filed: Mar. 15, 1990

[30] Foreign Application Priority Data

Mar. 24, 1989 [IT] Italy ................................ 5140 A/89

[51] Int. Cl.⁵ ............................................. G01N 21/00
[52] U.S. Cl. ..................... 356/339; 356/337; 422/58; 422/74; 436/23
[58] Field of Search ............................ 356/335–343, 356/246, 244, 435, 436; 436/20, 22, 23, 164, 149; 422/55, 58, 74

[56] References Cited

U.S. PATENT DOCUMENTS

| | | | |
|---|---|---|---|
| 2,844,067 | 7/1958 | Borg | 436/23 |
| 3,633,012 | 1/1972 | Wilhelmson | 422/55 |
| 4,400,353 | 8/1983 | Meserol et al. | 422/58 |

FOREIGN PATENT DOCUMENTS 0088432  4/1988  Japan ................................ 356/339

Primary Examiner—Richard A. Rosenberger
Assistant Examiner—Hoa Pham
Attorney, Agent, or Firm—Bucknam and Archer

[57] ABSTRACT

An optical measuring device for measuring the fat contents of milk comprises a light source, an optical condenser, a glass test tube provided for holding a set amount of the milk the fat contents of which must be measured, a lens, a photosensitive element, for example of the CCD type, and a digital display, all enclosed in a metal housing which also holds a control electric and electronic system, the fat contents of the milk being measured by detecting, by means of the photosensitive element, the diffusion depth of the light projected by the light source on the milk held in the test tube and reflected on the photosensitive element by the fat particles.

1 Claim, 1 Drawing Sheet 5,033,852

OPTICAL MEASURING DEVICE FOR MEASURING THE FAT CONTENTS OF MILK

BACKGROUND OF THE INVENTION

The present invention relates to an optical measuring device for measuring the fat contents of milk.

As is known, the milk fat contents is conventionally measured by means of optical sytems which are adapted to detect the diffused light coming from the fat particles of the milk: for carrying out this measurement, the milk must be previously homogenized by adding to the milk homogenizing substances adapted to generate in the milk particular phenomena, such as the so-called "trialton" phenomenon. However, the homogenizing step causes detection difficulties and, moreover, this step must be carried out by skilled persons.

The fat contents of the milk is also measured by conventional chemical measurement methods based on apparatus for measuring the volume amount of the milk fats: however, even in this case, skilled labour must be used.

SUMMARY OF THE INVENTION

The main object of the present invention is to provide a very simple, quick, reliable and unexpensive device for carrying out the above mentioned fat measurement, which is very important for example in the dairy production systems.

According to one aspect of the present invention, the above mentioned object, as well as yet other objects, which will become more apparent hereinafter, are achieved by an optical measurement device for measuring the fat contents of milk comprising a light source, an optical condenser a glass test tube provided for holding a set amount of the milk to be tested, a tubular housing for the milk test tube; a lens and a photosensitive element, for example of the CCD type, and a digital display, characterized in that the milk fat contents is measured by automatically measuring, by means of said photsensitive element, the diffusion depth of the light projected on a milk sample being measured.

The subject measuring device, in particular, provides the follwoing very important advantages;
the operation of the device is very simple;
it practically overcomes any measurement errors;
it does not require, for carrying out the fat measurement, that the milk sample be processed by homogenizing processes or additioned with reactive substances;
the milk samples to be measured can be prepared in a very quick and simple way;
the measurement can be carried out by unskilled persons;
the measurement cost is reduced to a minimum since the measurement requires a very small time;
it provides very accurate and reliable measurement results;
it can be easily serviced and cleaned.

BRIEF DESCRIPTION OF THE DRAWINGS

Further characterisitics and advantages of the device according to the present invention will become more apparent from the following detailed disclosure of a preferred embodiment thereof which is illustrated, by way of an indicative but not limitative example, in the accompanying drawing, where.

DESCRIPTION OF THE PREFERRED EMBODIMENT

Figure 1:
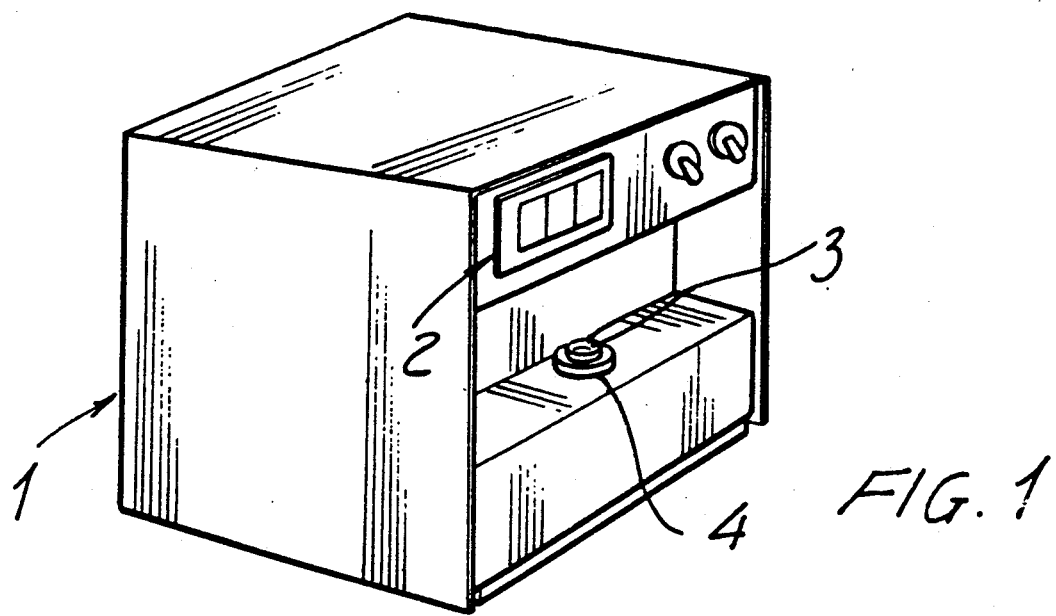
FIG. 1 is a side perspective view showing a possible embodiment of the milk fat measuring device according to the present invention.
Figure 2:
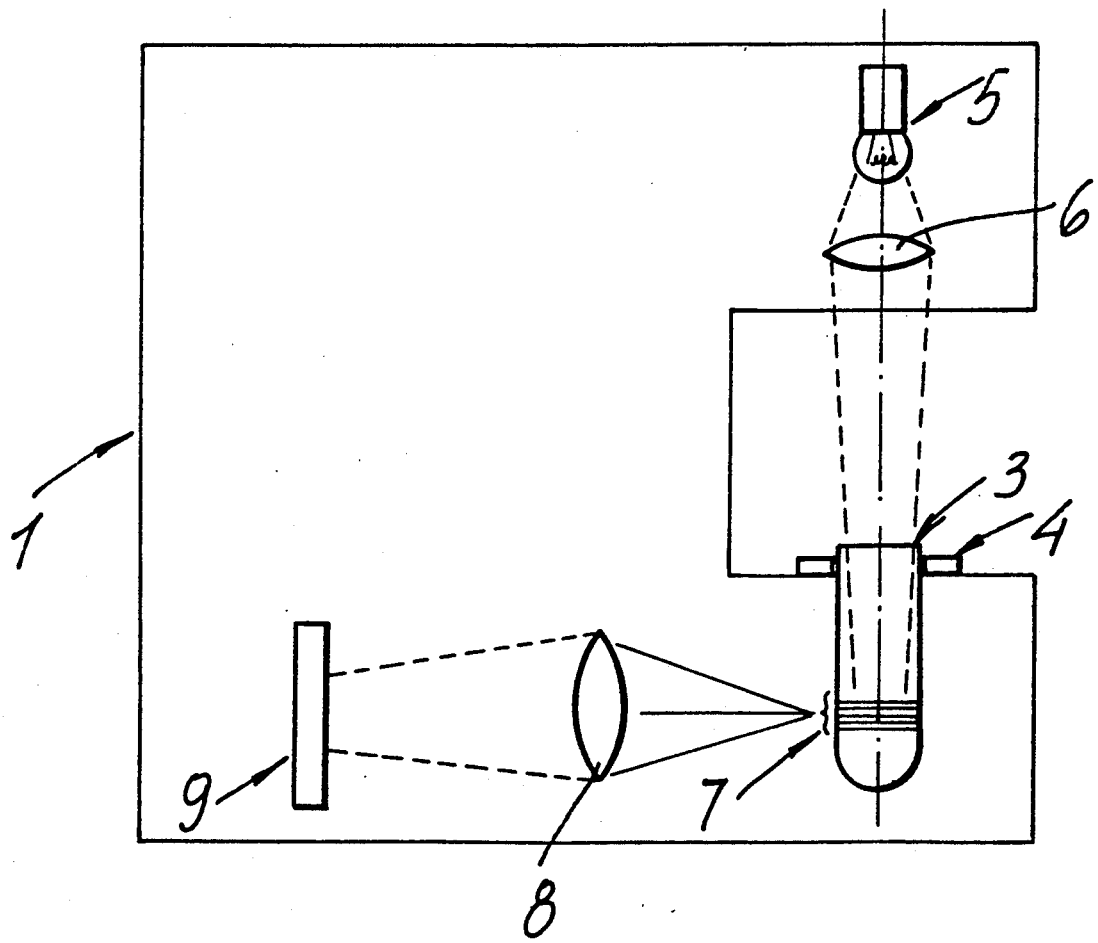
FIG. 2 schematically shows the main parts included in the measuring device according to the invention.

With reference to the figures of the drawing, the optical measuring device for measuring the fat contents of milk comprises a light source 5 (for example a lamp), a condenser 6, a glass test tube 3 provided for holding a set amount of the milk the fact contents of which must be measured, a tubular housing 4 for housing the glass test tube 3 said tubular housing having a closed bottom and a diameter adapted to precisely restrain therein in a precise vertical arrangement said test tube, a lens 8, a photosensitive element 9, for example of the CCD type, adapted to detect the penetration depth of the light from the source 5 in the milk held in the tube 3, and a digital display 2, so arranged as to fascilitate the read out of the measurement results.

The above disclosed parts are enclosed in a metal shaped housing 1 which also encloses all of the electronic components forming the electronic system, not specifically disclosed, for processing the milk fat measurement data provided by the subject measurement device, as it will become more apparent hereinafter.

For carrying out the fat contents measurements, the following steps must be carried out:

I—introducing into the glass test tube 3, in a cleaned and dry condition, an accurately metered set amount of the milk sample to be measured, by using a conventionl pipette which set milk amount will be defined by a level mark on the surface of the test tube;

II—arranging the glass test tube 3 in the seat or housing 4 in which said test tube will be held in a precise vertical position, so as to locate the top surface of the milk in said test tube at a set read-out level with respect to said lens 8 and photosensitive element 9;

III—switching on the lamp 5 so as to cause the light beam produced by said lamp to impinge on the free top surface of the milk held in the test tube 3. In this connection it should be pointed out that the light beam will be preliminarly concentrated by the lens 6 so as to properly impinge on the mentioned top surface of the milk held in the test tube;

IV—holding test tube and the milk contained therein always at the mentioned constant set level or position since the detection accuracy of the device will depend on said position. In this connection it should be apparent that the light depth penetration that is the intensity of the light reflected by the fat particles, will be inversely proportional to the number of the emulsified fat particles present in the milk sample, and this according to a logarithmic law;

V—directly projecting, by the lens 8, the light rays coming from the measurement zone or depth 7 and reflected from the fat particles on the photosensitive element 9, thereby the element 9 will provide electrical signals the intensity of which will be proportional to the intensity of the fat particle reflected light;

VI—electronically processing the electrical signal from said photosensitive element 9 to provide a measurement of the fat particles present in said zone 7 of the test tube 3 , and displaying the milk fat contents on the display 2;

VII—reading on the display 2 the value of the measured milk fat contents in conventional fat concentration units.

It should be apparent that the several detection and display signals will be suitably processed by the electronic system included in the device and which can be easily designed by one skilled in the electronic art.

While the invention has been disclosed and illustrated with reference to a preferred embodiment thereof, it should be apparent that the disclosed embodiment is susceptible to several modifications and variations all of which will come within the spirit and scope of the appended claims.

I claim:

1. An optical measuring device for measuring the fat contents of milk comprising a housing including, in a stacked arrangement, a light source, an optical condenser and a glass test tube provided for holding a set amount of milk therein, said test tube fitting in a tubular well provided in said housing and restraining said test tube in a precise vertical position, said light source including a lamp which can be energized for causing a light beam to impinge on said milk in said test tube, on said test tube there being provided at least a level mark indicative of set amount of milk in said test tube, a reflected light detecting assembly to detect light rays reflected by fat particles in said set amount of milk and provide electrical signals proportional to a penetration depth of said light beam from said light source into said milk, said detecting assembly including a lens arranged at bottom portion of said test tube near said at least a level mark and, in a substantially horizontal aligned arrangement with said lens, a photosensitive element adapted to convert said light rays reflected by said fat particles into electrical signals indicative of said penetration depth, processor means being moreover provided for processing said electrical signals from said photosensitive element provide to display means drive signals to cause said display means to display a concentration value of said fat particles in said milk.

* * * * *